United States Patent [19]
Markov

[11] Patent Number: 4,546,095
[45] Date of Patent: Oct. 8, 1985

[54] USE OF FRUCTOSE-1,6-DIPHOSPHATE FOR TREATING MYOCARDIAL INFARCTION

[76] Inventor: Angel K. Markov, 353 Northside Cir., Jackson, Miss. 39206

[21] Appl. No.: 414,551

[22] Filed: Sep. 3, 1982

Related U.S. Application Data

[63] Continuation of Ser. No. 170,614, Jul. 21, 1980, abandoned.

[51] Int. Cl.[4] .................... A61K 31/66; A61K 31/70; C12P 19/24
[52] U.S. Cl. ..................................... 514/23; 536/117; 435/2
[58] Field of Search ........................ 536/117; 424/180; 514/23

[56] References Cited
PUBLICATIONS

Melloni et al., "Chem. Abst.", vol. 59, 1963, p. 6816(g).
Burreno et al., "Chem. Abst.", vol. 83, 1975, p. 109527(s).
Schuler et al., "Chem. Abst.", vol. 85, 1976, p. 14363(n).
Markov et al., "American Heart Journal", vol. 100, No. 5, Nov. 1980, pp. 639-646.

*Primary Examiner*—Johnnie R. Brown
*Attorney, Agent, or Firm*—Pravel, Gambrell, Hewitt & Kimball

[57] ABSTRACT

The invention relates to the treatment of heart disorders. Disruption of heart action or occulision of heart artery results in oxygen deprivation and aerobic metabolism ceases. Unless effective treatment is administered acidosis renders anaerobic metabolism inactive and irreversible tissue damage occurs.

Fructose-1,6-diphosphate is used as a therapeutic agent for treating mammalian subjects experiencing myocardial infection in order to prevent ischemic tissue from irreversible tissue damage.

5 Claims, 7 Drawing Figures

MEAN ARTERIAL PRESSURE RESPONSES IN
FLUID DEPRIVED DOGS AFTER I.V. INJECTION OF
1 mg/kg OF ENDOTOXIN

USE OF FRUCTOSE-1,6-DIPHOSPHATE FOR TREATING MYOCARDIAL INFARCTION

This is a continuation of application Ser. No. 170,614, filed July 21, 1980, now abandoned, entitled "Medical Treatment Using Fructose-1,6-Diphosphate".

BACKGROUND OF THE INVENTION

1. Field of the Invention

The present invention relates to the methods of treatment of patients with heart disorders and more particularly to the method of using Fructose-1,6-Diphospate in treatment of the above mentioned diseases, and also as a protective agent against unforeseen catastrophic hypotension or hypoxia during operative procedures, and as a preservative agent for transplantation organs.

2. General Background and Prior Art

In medicine and physiology it is well-known that a continuous supply of energy is necessary for the function and maintenance of a living state by cells. The degree of intracellular energy is measured by the ratio of high energy phosphate compounds to those of less energy potential (i.e., adenosine triphosphate to adenosine diphosphate and adenosine monophosphate). The biochemical pathways which produce high energy phosphate compounds have been well established in the scientific literature as a chain of reactions that result in the breakdown of the major substrates, glucose or other sugars to pyruvic and lactic acid and is a process of carbohydrate metabolism. Although one stage of glycolysis requires oxidation by dehydrogenation, this may be accomplished without oxygen, so the process as a whole may be anaerobic. The pyruvic acid formed by glycolysis is then oxidized to carbon dioxide and water. This oxidation is the source of most of the utilizable energy (ATP) derived from carbohydrate metabolism. Glycolysis also yields some energy in the form of ATP which can be utilized for muscle contraction and other functions. This is particularly important during sudden strenuous exercise, when energy must be made available in excess of that which can be provided by oxidation processes.

The glycolytic process taking place in animal tissues involves the sequence of intermediates:

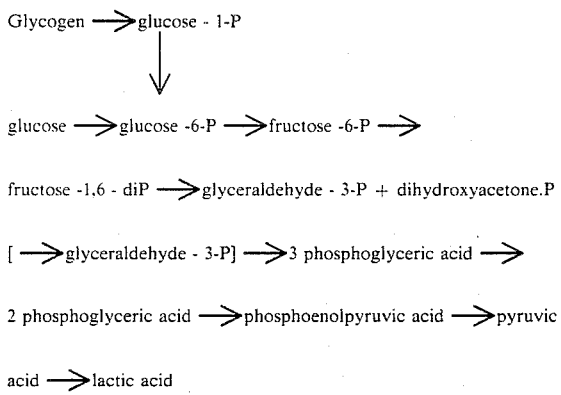

Fructose-1,6-diP is cleared by the enzyme aldolase between and third and fourth carbon atoms to form two triose phosphate molecules, glyceraldehyde-3-P and dihydroxyacetone phosphate.

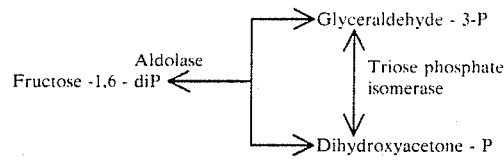

This reaction is reversible. Glyceraldehyde-3-P and dihydroxyacetone-P are freely interconvertible through the action of triose-P-isomerase.

The next step in the main stream of glycolysis consists of the combined phosphorylation and oxidation of glyceraldehyde-3-P to 1,3 diphosphoglyceric acid, which is catalyzed by the enzyme glyceraldehyde-3-P dehydrogenase:

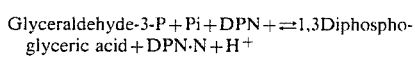

The conversion of glyceraldehyde-3-P to 1,3 diphosphoglyceric acid proceeds anaerobically through oxidation by $DPN^+$. In this process $DPN^+$ is converted to $DPN \cdot H$, and the reaction would soon cease without a mechanism to reoxide $DPN \cdot H$ to $DPN^+$, since the amount of coenzyme present is very small. Anerobically $DPN \cdot H$ is oxidized to $DPN^+$ by pyruvic acid, with the formation of lactic acid:

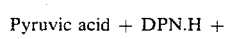

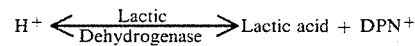

Substances other than pyruvic acid may serve also to oxidize $DPN \cdot H$ to $DPN^+$. Among these are dihydroxyacetone-P, which is reduced to α-glycerophosphate, and oxaloacetic acid, which is reduced to malic acid. Reduction by these substances is of importance in starting the glycolytic process before sufficient pyruvic acid has been formed to function in the regeneration of $DPN^+$. No ATP is formed in the oxidation of $DPN \cdot H$ by pyruvic acid.

When the supply of oxygen to the tissues and the oxidative mechanisms are adequate, the $DPN \cdot H$ is oxidized to $DPN^+$ through the mitochondrial electron transport chain:

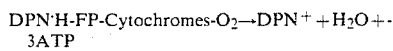

Consequently, lactic acid accumulates in tissues only when oxidation by $O_2$ cannot keep up with glycolytic reactions and pyruvic acid is reduced to lactic acid.

In this stage of glycolysis we have the first generation of utilizable energy as ATP. 1 molecule of ATP per triose phosphate mol when $DPN \cdot H$ is oxidized anaerobically (by pyruvate), and 4 mols per triose phosphate mol when $DPN \cdot H$ is oxidized by $O_2$.

The next stage of glycolysis consists in the conversion of 3-phosphoglyceric acid to 2-phosphoglyceric acid by the enzyme phosphoglyceromutase, which requires catalytic amounts of 2,3-diphosphoglyceric acid.

Glycolysis proceeds by the conversion of 2-phosphoglyceric acid to phosphoenolpyruvic acid through action of the enzyme enolase. This reaction involves dehydration of 2-phosphoglyceric acid and is freely reversible. The loss of water converts the low-energy phosphate group of 2-phosphoglyceric acid to the high energy phosphate group of phosphopyruvic acid. Because of the high energy phosphate group present in phosphopyruvic acid, it reacts with ADP to form ATP and pyruvic acid to complete glycolysis properly. The reaction is catalyzed by the enzyme ATP-phosphopyruvic transphosphorylase or pyruvic kinase, which requires $Mg^{++}$ and $K^+$ for activation. This reaction accounts for the formation of 2 mols of ATP per mol of sugar glycolyzed.

The reactions of glycolysis in animal tissues lead to the end products pyruvic and lactic acids. Pyruvic acid is oxidized and converted to acetyl CoA by an oxidative α-ketodecarboxylase enzyme. Oxidation of the DPN·H in the electron transport chain yields 3ATP per mol. The acetyl CoA formed from pyruvic acid is oxidized in the citric acid cycle to $CO_2$ and $H_2O$ with the formation of 12ATP per mol. So the aerobic pathway for the breakdown of sugars and fatty acids is dependent upon a ready supply of oxygen, which is provided to the body tissues through the bloodstream and is bound weakly to hemoglobin. Thus, interruption of either the pumping action of the heart occlusion of one of the arteries or failure to oxygenate the blood being circulated by the lungs will result in either a regional or generalized unavailability of oxygen.

If oxygen is not supplied to living tissue for any of the above mentioned reasons, aerobic or oxygen dependent metabolism ceases. This leads to an attempt to compensate the failure in oxygen supply by an increase in the rate of anaerobic metabolism.

It was already noted that the anaerobic metabolic pathway for carbohydrates involves glucose which then becomes phosphorated (has six-carbon sugar). These molecules then break down to trioses (three-carbon sugars) and enter the aerobic pathway as the pyruvate molecule. In tissues that have limited blood supply or, for some other reason fail to be given an adequate amount of oxygen, the aerobic pathway must provide all of the energy necessary for cellular function. However, during any form of oxygen deprivation, whether it is from heart attack or from blood loss, leading to hypoperfusion as in an injury, the pathways of metabolism are refractory to the further entrance of the glucose into the cell, and the critical breakdown point in the metabolic pathway is at the phospho-fructo-kinase enzyme step. This means that unless something different is done, the individual deteriorates to the point where his tissues are unable, because of the injury, to regain function which may lead to a fatal outcome.

Investigations have been made on the effect of sugars on the recovery of heart functions. For example, Dr. Pasi Kettunen of Finland described his experiments on the "Comparison of the Effect of Glucose and Fructose on the Recovery of the Heart Preparation" (Scand. j. clin. Lab. Invest. 37, 705–708, 1977). Potassium citrate solution was used for heart arrest, and heart function was recovered by infusion of Locke's solution, plus glucose, fructose or sucrose. During recovery period, the amplitude and frequency of heart beats, the lactic acid in the drained perfusion solution, pH and potassium concentration were measured. The use of glucose, fructose or sucrose made no significant difference to any of these parameters. Next, the metabolism of glucose and fructose in the heart was investigated and on a metabolic basis the use of glucose for resuscitation would seem to be more appropriate than fructose.

Dr. L. H. OPie and P. Owen in their investigation of glycolysis in acute experimental myocardial infarction found out that glycolysis during anaerobic circumstances may be accelerated by all the factors that stimulate phosphofructokinase activity. They indicated that there is an overwhelming change that may be expected to inhibit phosphofructokinase activity, namely the intracellular accumulation of hydrogen ions. This phenomena was confirmed by Ui in 1960 and Kübler and Spieckermann in 1970. Dr. Opie then wrote that some index of phosphofructokinase activity can be obtained by measurements of tissue contents of glucose-6-diphosphate. Glycolytic flow may be compared to a regular stream, phosphofructokinase acts as a am-wall, inhibiting the flow of glycolysis. Thus it is evident that these investigations, being valuable by themselves could not provide a sufficient method and an agent which can modify energy requirements intracellularly in the fact of low oxygen levels, poor blood circulation or poor distribution of circulation.

GENERAL DISCUSSION OF THE PRESENT INVENTION

As it has been mentioned above, the biological attempt to compensate for insufficiency of aerobic metabolism leads to a temporary increase in the rate of anaerobic metabolism, but this compensatory mechanism is limited by acidosis of the involved tissues. Once the inevitable acidosis occurs, this pathway is inactivated also. The premature shutdown of the anaerobic pathway is not an irreversible phenomena, rather the effect of acidosis from lack of oxygen causes interruption at several critical steps. First, glucose cannot gain access to the cellular interior. Next, phosphofructokinase, the enzyme which catalyzes the conversion of fructose, 6, monophosphate to fructose 1,6, diphosphate is rendered inactive.

To bypass these metabolic bottlenecks, fructose 1,6 diphosphate can be injected in amounts exceeding substantially that which could be available in the natural state. This sugar, if metabolized to lactic acid, will produce 4 molecules of ATP without the requirement of oxygen. Besides, the fructose molecule unlike glucose does not require energy to cross the cell membrane and is not dependent upon the action of insulin and it enters above the PFK enzyme level which has been damaged during the ischemic process. Therefore, the addition of fructose 1,6 diphosphate appears to be a significant step in by-passing this and obtaining temporary energy to sustain ischemic tissues, perhaps even the whole organism over a limited time while it is being infused. It may produce from 20 to 80 percent of the energy required for a given tissue. In a number of experiments which have been carried out by Dr. Angel Markov, in the Department of Medicine at the University of Mississippi, it has been shown repeatedly that the material is useful when given in hemorrhagic shock, experimental myocardial infarction, and other conditions where tissue is without oxygen. In Dr. James W. Jones' experiments, it has appeared that this material is very useful in metabolism of the heart. The research gives an evidence that the material could be useful in treating patients with the following disorders:

1. Hemorrhagic shock;
2. Cardiogenic shock;
3. Cyanide poisoning and any poisoning of oxidative metabolism;
4. Myocardial preservation;

5. Therapeutic agent after myocardial infarction;
6. During respiratory failure with low blood oxygen levels;
7. During operative procedures as a protective agent against unforeseen catastrophic hypotensive or hypoxia;
8. As a preservative agent for transplantation organs such as a kidney, liver, heart, etc.;
9. As an agent to enhance drugs it would be given as chemotherapeutic agents to destroy a tumor cell;
10. Sickle-Cell anemia;
11. Reversal barbituate overdose;
12. Blood preservation;
13. As an agent for treating disorders in white blood cells' phagocytosis; and
14. Endotoxin shock.

In the experiments regarding an irreversible hemorrhagic shock, results were obtained in the dog model using Wigger's modified technique. We compared a group of animals receiving IV administration of fructose-1,6-diphosphate (FDP) to a group receiving equimolar glucose.

The metabolic changes resulting from generalized tissue hypoxia revealed alteration in the acid base balance and increased lactic acid concentration in blood reflecting the relatively anaerobic character of the metabolism. The rate of anaerobic glycolysis for different tissue appears to be a direct function of the severity of hypotension and the severe hypotension could accelerate glycolysis in the heart and other organs by 100% when compared to control. Although there is an initial increase of anaerobic glycolysis after a certain period, its rate begins to decline due to progressively increasing acidosis secondary to increased lactemia.

The phosphorylation of fructose-6-phosphate is an important control point in the Embden-Meyerhof pathway. Phosphofructokinase (PFK) is a multivalent enzyme which catalyzes this rate limiting reaction. PFK is stimulated by ADP, AMP and FDP and inhibited by ATP, citrate and acidosis. It is already known that the ischemic inhibition of glycolysis is due to inactivation of PFK by progressively increasing intracellular acidosis. As is shock severe metabolic acidosis takes place, it is reasonable to assume that PFK is inactivated. This is substantiated by the observation that in hemorrhagic shock plasma lactate initially increases very rapidly and then lactate production appears to decline. In out experiments the plasma lactate measured at 2 hrs 45 min after the onset of hypotension in the controls was found to be $76 \pm 14$ mg %, while in dogs treated with FDP that concentration was in the order of $124 \pm 16$ mg %.

Our experiments also gave evidence that serious cardiac failure (secondary to impaired energy production) occurs approximately at the time when hemorrhagic shock becomes irreversible and it is probably responsible for the fatal outcome of the condition. It is realized that the pathogenesis of hemorrhagic shock is a complex phenomenon in which every structural unit in the entire organism is affected (to different degrees). Yet, the circulatory weak spot contributing to the irreversibility of the hemorrhagic syndrome appears to be the heart itself. Forty years ago Wiggers realized that in the course of hemorrhagic shock, a deficit in coronary blood flow that arises could be implicated as a major cause for the irreversibility of the condition.

In control animals during the late course of the hemorrhagic shock changes were observed in metabolism in the endocardium taking place to be similar to those observed in acute myocardial ischemia. These are manifested by ST segment elevation which occurred in all non-treated animals and depletion of ATP and CP in the endocardium to the same degree as found in acute myocardial infarction.

To allow for a broader and more complete interpretation of the results, a small paragraph will be devoted to the ability of FDP to cross the cellular membranes. Although the actual mechanism of trans-membranous passage of FDP is not known, there is direct and indirect evidence which substantiate that it crosses through cellular membranes. These data are consistent with the modern concept of the membrane which is capable of transferring high energy substrate through a series of coupled reactions. From experimental data, indirect evidence substantiates the assumption that FDP crosses the cellular membrane in different tissues in animals and man. In isolated organs, for example, when FDP is added perfusate, rabbit ileum increases the force of contraction, while glucose-6-phosphate, fructose-6-phosphate or fructose and inorganic phosphate fail to produce the same effect. This effect of FDP on rabbit ileum can be correlated with the increased availability of ATP and the regulatory effect of FDP or PFK, on pyruvate kinase and in inhibition of 6-phosphogluconate dehydrogenase. As all of these enzymes are in the cytoplasm, FDP must cross the cellular membrane in order for such an effect to be observed. Incubation of erythrocytes with 5% FDP causes a large increase in their ATP and 2-3 DPG content. Equimolar glucose, glucose-6-phosphate, fructose-6-phosphate, fructose and inorganic phosphate failed to increase the ATP content in the erythrocytes incubated under the same conditions. Intracardiac administration of FDP in rat causes five times higher concentration of FDP in the liver than in plasma 10 min after administration. Intravenous administration in dogs of 5 g of FDP over 10 min causes the plasms lactic acid (measured at one hour) to increase $2\frac{1}{2}$ times (from $6.13 \pm 1.7$ to $16.45 \pm 2.16$ mg %). In other experiments we have found that IV administration of FDP causes an increase of ATP, lactate, and FDP in all tissues that we have studied, as well as increases in the trioses in the Embden-Meyerhof pathway.

We attempted to remove the inhibition of PFK, hence glycolysis, in the shock model described in intravenous administration of FDP, thus increasing energy production, preventing cardiac damage and improving survival. Fructose diphosphate in the described shock model reduced mortality to zero, prevented electrocardiographic ischemic changes and increased significantly the ATP and CP in the endocardium. These changes were associated with accelerated glycolysis seen by increased plasma lactate and myocardial tissue lactate.

From an energetic point of view the advantage of using FDP as the initial substrate is that the net yield of the anaerobic metabolism of one mole of glucose is 2 ATP, while if one mole of FDP is metabolized in the same conditions it will produce 4 ATP because there is no phosphorylation of glucose and fructose-6-phosphate reactions which require utilization of ATP. On the other hand, while doubling the quantity of ATP produced, lactate production remains the same as though one mole of glucose had been metabolized. It is obvious that in order to obtain results in the direction of making usuable energy from FDP, it is necessary to administer a large quantity. (The $LD_{50}$ of FDP when administered 500 mg/min in dogs is approximately 5.8–6 g/kg.)

Another important metabolic effect of FDP is that it causes a substantial increase of ATP and 2-3 DPG in the erythrocytes. This increase of 2-3 DPG is of importance for the oxygen exchange between hemoglobin and tissue. It may also contribute in part to energy production derived from the oxidative metabolism by increasing the oxygen availability to tissues in such a low flow state.

The significance of the present invention is not only limited to the successful treatment of experimental irreversible hemorrhagic shock by increasing metabolic activity of glycolysis, but as well it proposes a unifying concept for understanding the pathophysiological mechanism of shock. There is no doubt that the nature of the initial insult is irrelevant to the genesis of shock, but what is important is the fact that the organism as a whole integral unit shares with its constituents (organs and cells) a common energy deficit. In the early stages of any etiologic type of shock there is inadequate oxygen transport and supply to tissue. Hence, there is an energy deficit. Every system, organ and individual cell responds to this decrease in energy supply according to their entropic state. As the biological system is an open system, any deficit in free energy would be manifested by increasing the disorder of the system and as in shock the vicious cycle is initiated which leads the system to higher and higher degrees of disorder. The final stage of this intracellular disorder is the achievement of the same entropic state between "milieu exterieur" and "milieu interieur"—defined in biological terms as death.

It is thus an object of the present invention to provide a method of treating patients during a hemorrhagic shock by fructose-1,6-diphosphate (FDP).

It is another object of the present invention to provide a method of treating patients in cardiogenic shock with FDP.

It is a further object of the present invention to provide a method of treating patients in case of cyanide poisoning by FDP.

It is another object of the present invention to provide a method of myocardial preservation by treating a patient with FDP.

It is a further object of the present invention to provide a method of treating patients after myocardial infarction by using FDP as a therapeutic agent.

It is still another object of the present invention to provide a method of treating patients with FDP during respiratory failure with low blood oxygen levels.

It is a further object of the present invention to provide a method of introducing FDP during operative procedures so that it might be a protective agent against unforeseen catastrophic hypotension or hypoxia.

It is still another object of the present invention to provide a method of preservation of transplantated organs using FDP as a preservative agent.

Still another object of the present invention is to provide a method of treating cancer patients by using FDP as a possible means of causing damage to the tumor cells and using it as a chemotherapeutic agent to enhance drugs in destroying tumor cells.

It is further an object of the present invention to provide a method of treating patients with FDP during a sickle cell crisis.

Still another object of the present invention is to provide a method of treating patients having a reversal barbituate overdose.

Another object of the present invention is to provide a method of using FDP for blood preservation.

It is another object of the present invention to provide a method of treating patients with disorders in white blood cells' phagocytosis using FDP.

Finally, another object of the present invention is to provide a method of treating patients with FDP during an endotoxin shock.

BRIEF DESCRIPTION OF THE DRAWINGS

Of further understanding of the nature and object of the present invention, reference should be had to the following detailed description, taken in conjunction with the accompanying drawings, in which like parts are given like reference numerals and, wherein.

DETAILED DESCRIPTION OF THE PREFERRED EMBODIMENT

Figure 1:
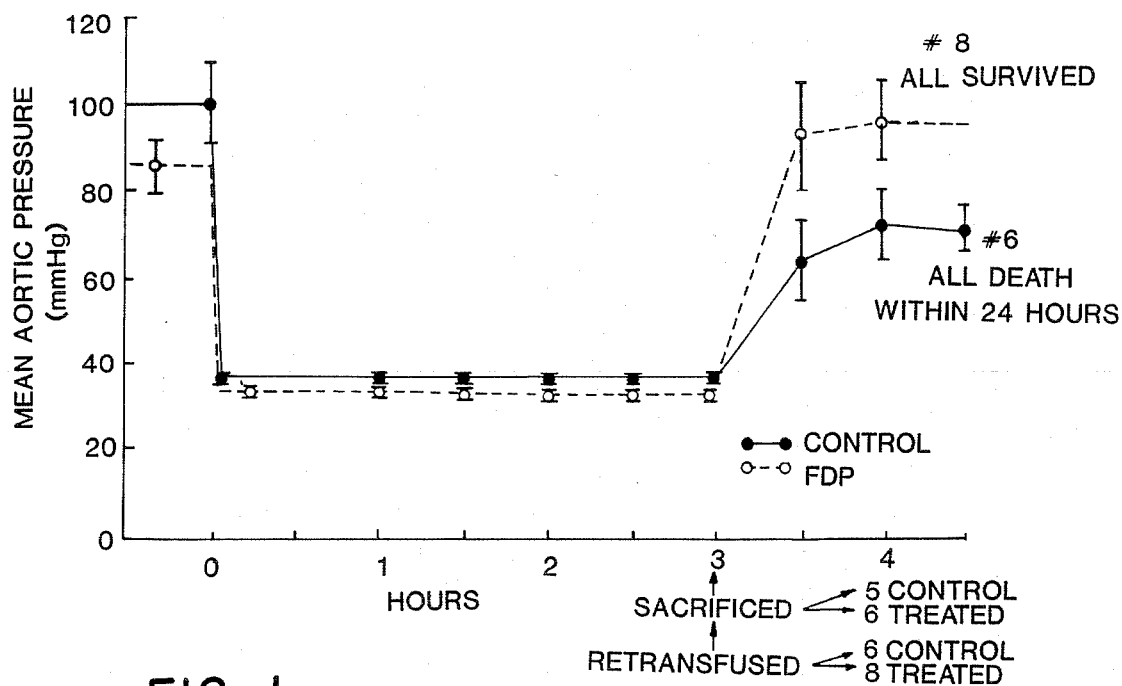
FIG. 1 would illustrate mean arterial pressure responses of dogs subjected to hemorrhagic shock for three hours at 33 mm. Hg.

The drug is a sugar diphospate compound that needs to be injected intravenously in both a bolus form or a single dose or as multiple single doses or as a continuous infusion drip. The amounts to be given should not exceed 5 grams per kilogram body weight per hour in infusion. If the heart alone is having it infused then it would be per kilogram per tissue. This adjustment must be made because the drug has detrimental affects with a LD 50 or a lethal dose of 50% of the animals given if this is exceeded. The dosages which have been useful are to give 50 ml per kilogram body weight in a single dose or to give 1.5 to 2 ml per kilogram of body weight over each minute as in continuous infusion.

We shall first discuss the method of treating of a hemorrhagic shock. The sequence of events following severe hemorrhage is believed to be: decreased venous return, decreased cardiac output, reduced arterial pressure, decreased blood flow to the organs with ensuing tissue hypoxemia. Hemorrhagic shock, therefore, represents acute circulatory insufficiency that leads to generalized tissue ischemia. Studies directed at the possible deleterious effects of the metabolic derangements or tissue products resulting from reduced flow in shock have revealed alterations in the acid base balance, and chemical composition of the blood reflecting the relatively anaerobic character of metabolism in shock. The degree of metabolic acidosis, increased plasma and tissue lactate in hemorrhagic shock are functions of the severity of the hypotension. Although there is an increased rate of anaerobic glycolysis and plasma glucose initially, after a certain period its rate begins to decline due to the progressively increasing acidosis caused by the increased lactate production. This progressive inhibition of the Ebmden-Meyerhof process by acidosis appears to be caused by the inactivation of the pH acid sensitive rate limiting enzyme of glycolysis, phosphfructokinase (PFK).

During the late phase of hemorrhagic shock, morphological and metabolic changes that take place in the endocardium are similar to those observed in the course of acute myocardial ischemia. Cardiac failure may occur in hemorrhagic shock secondary to a deficit in coronary blood flow. The hemorrhagic state becomes irreversible due to impairment of cardiac function. In view of this, the goal of the present invention was concerned with the evaluation of the therapeutic value of fructose-1,6-diphosphate in preventing death and cardiac damage when administered during the oligemic phase of shock which has been shown to be irreversible to the infusion of all shed blood. We regard this as the most valid technique for testing the efficacy of this agent.

The experiments were performed in 25 pentobarbital anesthetized (30 mg/kg IV) mongrel dogs of both sexes. After induction of anesthesia the animals were intubated and ventilated with a Harvard respiration pump with the use of ambient air. Secured in the left lateral decubitus position on the fluoroscopic table, a femoral artery was used to introduce a large bore polyethylene catheter which was connected to a 1.5 liter bottle elevated at 35 mm Hg above the atrial level. In the connecting system an external calibrated electromagnetic flow probe (Statham) was incorporated in order to follow the direction and amount of blood flow. The pressure in this system was monitored through a side opening with the aid of a Statham pressure gauge. The other femoral artery was percutaneously catheterized and a Judkins type pigtail catheter was advanced to the aortic root. In the course of the experiments this catheter was placed intermittently into the left ventricle when recordings were made. This set-up enabled us to monitor both aortic and left ventricular pressures via a single catheter. The femoral vein on the side where the incision was made was catheterized as well as a superficial vein of the front limb transutaneously for administration of the FDP, glucose, heparin and supplemental anesthetic. Parameters such as aortic, ventricular and femoral pressures, and EKG were monitored on an Electronics for Medicine DR-8 recorder. Recording of these parameters was made every 15 min. Heparin (6 mb/kg initially and thereafter 3 mg/kg/2 hrs) and antibiotics were given to all animals that were allowed to recover. A control period of one hour was allowed prior to bleeding the animal. During this period two arterial blood samples were drawn for pH, $pO_2$, $pCO_2$, $pCO_2$ combining power and lactic acid determinations. During the oliegemic phase four arterial samples were taken for determination of the same parameters described at 30 min, 1 hr, 2 hrs and 2 hrs 45 min.

The blood from the animals was withdrawn via the femoral artery (50–55 ml/min) until the mean arterial pressure dropped to 35 mm Hg and from then on the pressure was kept at this level for three hours. The protocol for evaluating the therapeutic effect of FDP was designed in the following manner. The 11 control animals received an IV bolus of 500 mg of glucose when the mean arterial pressure was stabilized at 35 mm Hg, and thereafter, a constant infusion of 5% glucose was given at the rate of 1.25 mg/kg/min. The treated dogs received FDP (fructose-1,6-diphosphate sodium salt, Sigma Chemical, Grade II) 500 mg as an initial bolus and constant infusion of a 5% solution at a rate of 1.25 mg/kg/min. Both groups received an additional 500 mg IV bolus of FDP or glucose every 30 min for the duration of the oligemic phase. In five controls and six treated dogs the chest was opened at three hours and with the aid of specially designed cutting tool that had been cooled in liquid nitrogen, frozen transmural sections from the left ventricle were taken for ATP, creatine phosphate (CP), FDP and lactic acid determinations. The remaining 14 animals (6 controls and 8 treated with FDP) were retransfused at three hours and allowed to recover.

The epicardium and endocardium from the frozen tissue were separated (while still frozen) and homogenized in 6% perchloric acid. The supernatant was used to determine ATP, CP and lactate. The ATP and creatine phosphate were assessed with the method described by Lamprecht (Lamprecht, W., and P. Stein. Methods of Enzymatic Analysis, Ed: H. V. Bergmeyer, New York, Academic Press, 1963, p. 610.) while lactate was measured by the method of Marbach (Marbach, E. P., and M. H. Weil. Rapid enzymatic measurement of blood lactate and pyruvate. Clin. Chem. 13: 314, 1967). Tissue content of FDP was assessed by the method of Bucher and Hohorst (Bucher, T., and H. J. Hohorst. Dihydroxyacetone phosphate, fructose 1–6 diphosphate and D-glyceraldehyde 3-phosphate. In: Methods of Enzymatic Analysis. Ed: Bermeyer, New York, Academic Press, 1963, pgs. 246–252.)

In the initial phase of the hypovolemia there was continuous outflow of blood into the reservoir. The level of blood was constantly monitored so it never exceeded 35 mm Hg above the atrial level. An overflow system prevented the level of blood from rising too high. However, after approximately $1\frac{1}{2}$ hours the blood flow reversed itself spontaneously (from the bottle to the animal) in the animals of the control group. In the group treated with FDP, only two of them reversed their flow at 2 hrs and 15 min and 2 hrs and 37 min. The amounts of blood uptake in these animals were 24% and 17% respectively of the shed blood.

In both groups the heart rate increased. In the control group the heart rate exceeded 225 beats/min. while for the treated animals the heart rate returned faster towards control (after retransfusion) and did not reach 200 beats/min. In both groups a substantial metabolic acidosis developed, though to a lesser degree in the control group. It was not exceptional in the group treated with FDP to find arterial pH of 6.8 and lower. The arterial plasma lactic acid concentration after the onset of hemorrhage increased rapidly for both groups. However, after 2 hours in the control group the lactic acids production began to level off contrary to the group treated with FDP where the plasma lactate continued to rise. In the control group, the plasma lactate concentration measured at 2 hours and 45 minutes was $76\pm14$ mg %, while in the dogs treated with FDP the plasma lactate at that time was in the order of $124\pm16$ mg %. The arterial pressure of the 14 animals that were allowed to recover (6 controls and 8 treated with FDP) measured at $1\frac{1}{2}$ hours after retransfusion demonstrated a striking difference.

All control animals demonstrated ischemic EKG changes on precordial leads (always between 55 min and 1 hour and 15 minutes after the onset of shock). The ST elevation reached maximum at 2 hours (0.55±0.17 mV) and remained such until retransfusion when it began to decline. In contrast, in the group that was treated with FDP, only minimal elevation was observed in two animals. (N.B. In one of these dogs unintentionally FDP was not administered until 30 minutes after the onset of the hypotension and in the other animal the infusion pump had stopped for approximately 25 minutes.) In both animals after FDP was given the ischemic changes disappeared. The endocardial ATP content in the group that received glucose fell by 50% while the creatine phosphate (CP) in the epicardium and endocardium was 64% and 88% respectively less than normal. The animals treated with FDP revealed normal ATP myocardial content and no transmural gradient; however, in the endocardium there was 18% less CP than normal and no deficit in the epicardium. The endocardial/epicardial tissue lactate ratio for the group that received glucose was 1.52±0.21, and for those treated with FDP, 2.26±0.26. All 6 control animals that were retransfused died within 24 hours. All 8 dogs treated with FDP survived, had normal renal and bowel function and no neurological deficit was noted. All animals treated with FDP were kept for six months after the experiments except for one which had to be sacrificed at 1½ months after the experiment because of a gangrenous hind leg on the side where the femoral artery was used for bleeding.

In FIG. 1, best shown are mean arterial pressure responses of dogs subjected to hemorrhagic shock for 3 hours at 35 mm Hg. The tests showed that: (1) Irreversible experimental hemorrhagic shock of 3 hour duration at 35 mm Hg AP could be successfully treated with FDP. (2) Intravenous administration of FDP restores ATP and CP content in the myocardium, prevents the EKG ischemic changes and improves the myocardial contractility. (3) FDP restores the depressed activity of glycolysis in the endocardium induced by inactivation of PFK.

To evaluate the effect of FDP on global ischemia, 14 mongrel dogs were placed on cardiopulmonary bypass and their hearts were subjected to normothermic arrest for one hour. Seven animals had 50 l ml. of 5% glucose in 0.9% NaCl infused into the base of the aorta at 0 minutes, 20 minutes and 40 minutes following cross-clamping and, systemically, during reperfusion. The remaining 7 animals were treated identically except that 50 mg. of FDP was given instead of glucose and 2 mg/kg/minute was infused systemically during reperfusion. Hemodynamic measurements were taken before ischemia and at 15 and 30 minutes following reperfusion using an isovolumetric technique.

CONCLUSIONS

Intra-aortic and systemic administration of FDP has a profound effect on myocardial performance following severe ischemia. Both contractility and compliance are vastly improved during the recovery period.

FIG. 2 summarizes the hemodynamic and electrocardiographic effects of FDP when given to dogs with acute regional myocardial ischemia at 45 minutes after the occlusion of a coronary artery. (The decimal points for the left ventricular end-diastolic pressure are not visible; however, the scale is to 17.5 mm. Hg.) The FDP administration began at 45 minutes after the onset of ischemia and continued throughout the experiment as a constant infusion at the rate of 1.25 mg./kg/min.

Figure 3A:
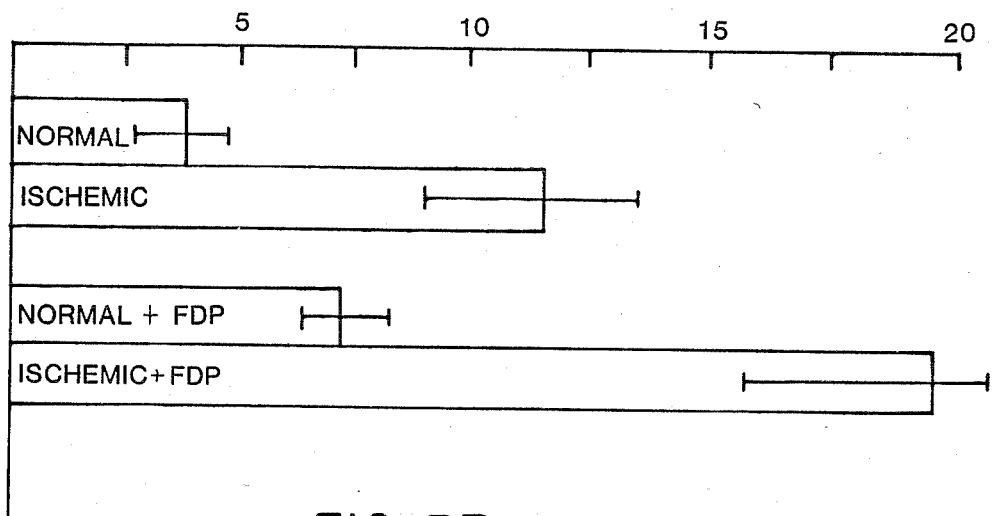
FIG. 3 would illustrate the adenosine triphosphate (ATP), creatine phosphate (CP) and tissue lactate content in the normally perfused and ischemic myocardium in both controls and FDP treated dogs.
Figure 3B:
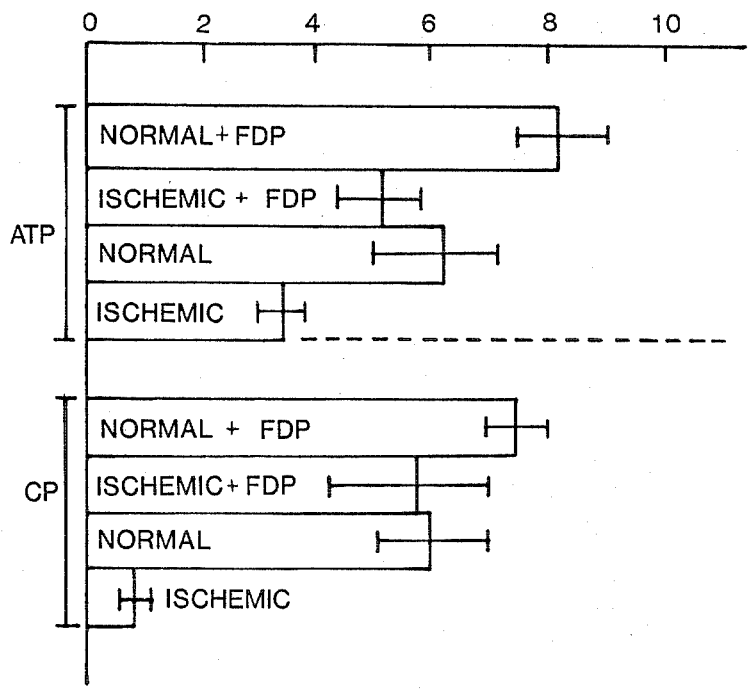

FIG. 3 shows the adenosine triphosphate (ATP), creatine phosphate (CP) and tissue lactate content in the normally perfused and ischemic myocardium in both controls and FDP treated dogs. Note that FDP not only caused an increase of ATP and CP in ischemic myocardium, but also in the normally perfused heart muscle. The same phenomenon was observed for the tissue lactic acid concentration.

Figure 4:
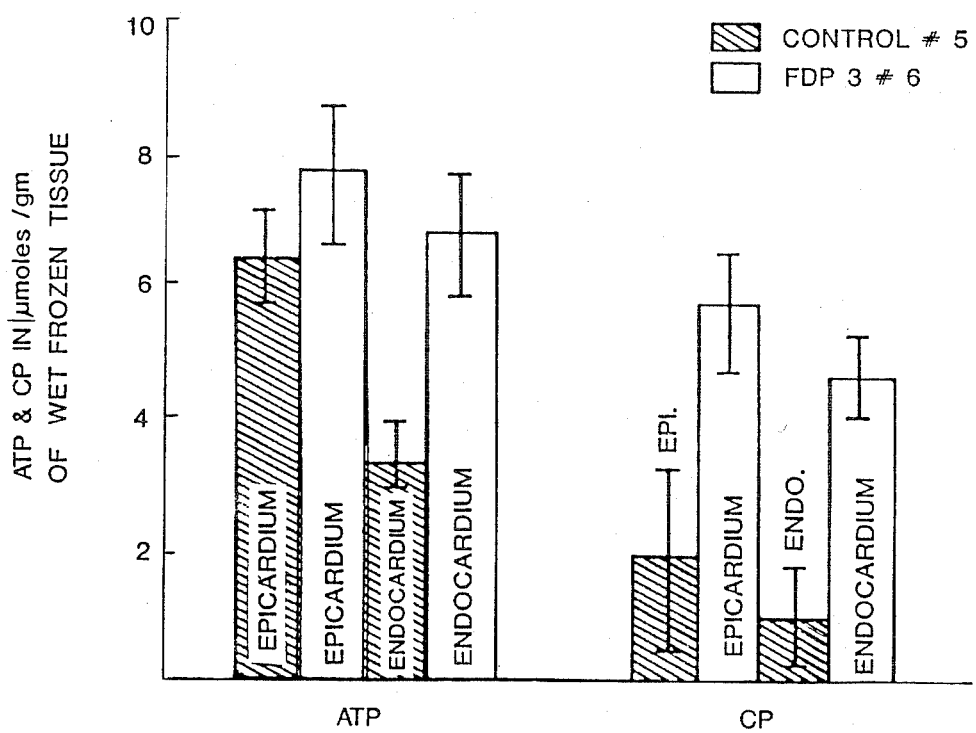
FIG. 4 would illustrate the Adenyl nucleotide content in the myocardium after hyptension of 35 mm. Hg. for 3 hours.
Figure 2A:
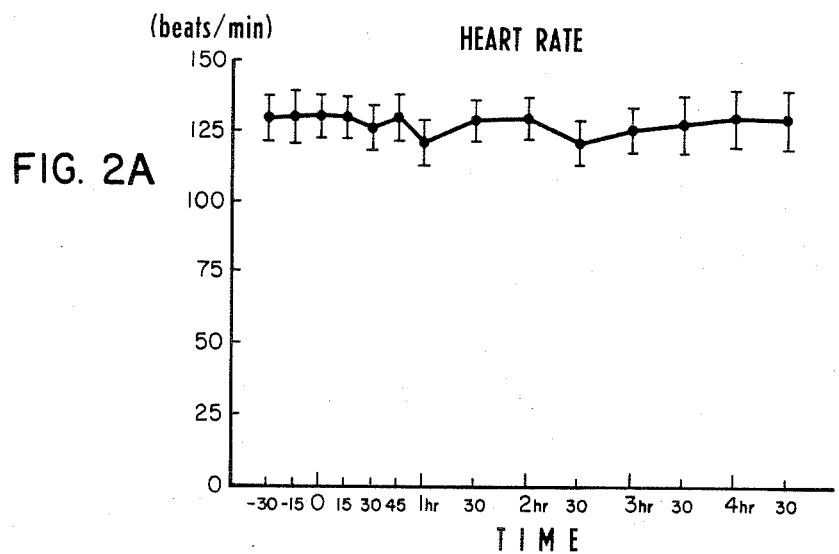
FIG. 2 would illustrate the hemodynamic and electrocardiographic effects of FDP when given to dogs with acute regional myocardial ischemia at 45 minutes after the occlusion of a coronary artery.
Figure 2B:
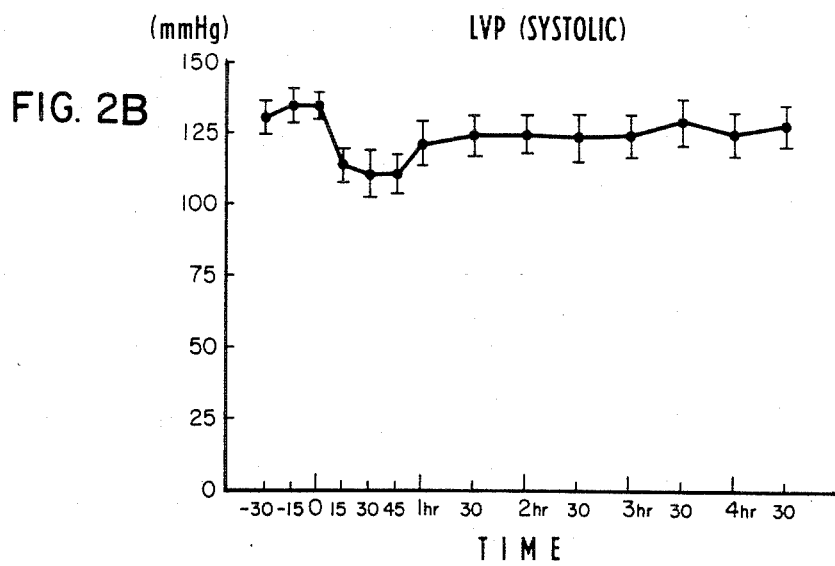
Figure 2C:
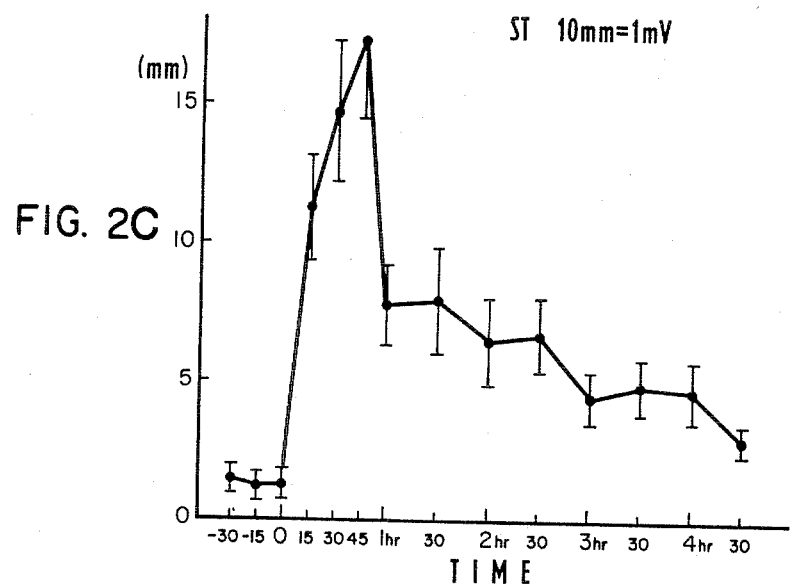
Figure 2D:
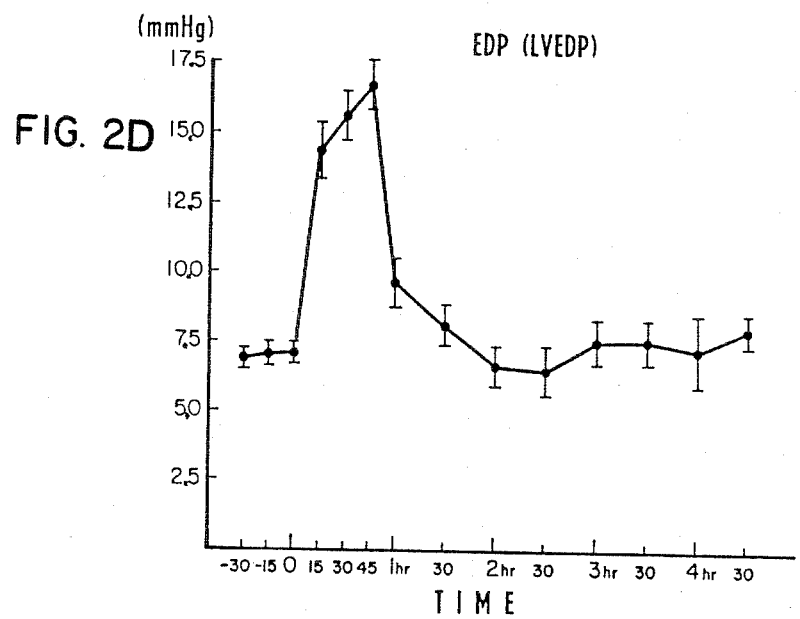
Figure 2E:
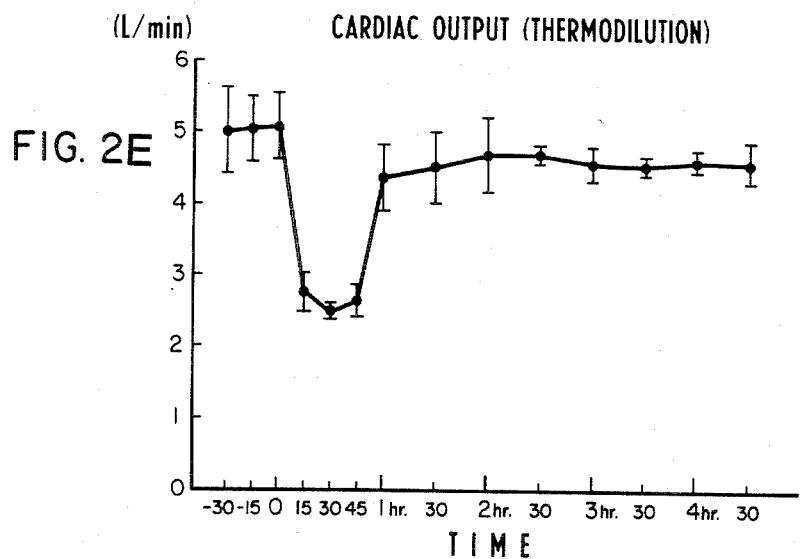

FIG. 4 shows the Adenyl nucleotide content in the myocardium after hypotension of 35 mm. Hg. for 3 hours. Note that in the epicardium in both controls and those treated with FDP there is no significant difference in ATP content while in the endocardium the ATP content reached values compatible with acute myocardial ischemia. FDP administration also prevents depletion of creatine phosphate (CP) in both epicardium and endocardium.

To explain the mechanism of using FDP as an antidote for potassium cyanide poisoning, we should note that potassium cyanide, or more precisely, the cyanide ion is a highly toxic substance which inhibits specifically the oxidation metabolism by inactivating the cytochrome a3 in the electron transfer chain. In such a circumstance the anaerobic glysolysis for a short period tries to compensate for the energy deficit by enhancing its activity. However, it can only partially meet the energy demand of the organism. As is has already been specified, FDP is a high energy intermediate of the Emden-Meyerhoff pathway and when used as an initial substrate in this metabolic pathway it will double its efficiency. In dogs, 2 mg/kg IV bolus injection of potassium cyanide was given and immediately they were treated with either FDP or Dextrose 5%. The dogs receiving 0.5 gm/kg over 30 minutes survived while the controls receiving the same amount of Dextrose died. Thus, it can be concluded that FDP could be employed as an antidote for acute potassium cyanide poisoning.

|  | Pre-Ischemia | | 15 minutes after | | 30 minutes after | |
| --- | --- | --- | --- | --- | --- | --- |
|  | Glucose | FDP | Glucose | FDP | Glucose | FDP |
| ML to LVEDP of 20 mm Hg. | 51.4 ± 8.6 | 39.3 ± 3.2 | 23.3 ± 1.8 | 33.6 ± 3.7* | 19.3 ± 1.3 | 36.1 ± 3.3** |
| Peak dp/dt (mm Hg/sec) | 4894 ± 689 | 4710 ± 689 | 1126 ± 216 | 2242 ± 226** | 1698 ± 350 | 3999 ± 404** |
| Peak Effective pressure (mm Hg) | 144.6 ± 14.6 | 165 ± 12.9 | 36.9 ± 4.4 | 102.1 ± 11.5** | 50.8 ± 6.3 | 125 ± 11.5** |
| Peak Mean pressure (mm Hg) | 66.4 ± 7.4 | 77.5 ± 4.6 | 17.8 ± 4.2 | 52.8 ± 5.4* | 20.5 ± 2.9 | 61.4 ± 5.1** |

*p 0.05
**p 0.01

Referring now to the use of FDP as an anesthetic barbiturate it should be specified that experimentally it has been demonstrated by Dr. Siesjo Harp, Jr. BK of the Netherlands that barbiturates when given in anesthetic concentrations cause a significant decline in carbohydrate utilization by the brain.

In our studies it was noted that the dogs receiving FDP (n=104) required twice as much anesthetic to be maintained in a state of surgical anesthesia as did the controls (n=103). Hence, the test was undertaken to evaluate more objectively the analeptic effect of intra-arterial administration of FDP on Surital (thiamylal) anesthesia in dogs.

In this paired test 10 dogs were anesthetized with Surital 35 mg/kg IV. Within 10 minutes after induction of anesthesia, a #7 Sones catheter was placed in a common carotid artery via the femoral artery under fluoroscopic guidance. Injection of contrast media verified that the position of the catheter did not obstruct the vessel, and portions of the brain were opacified transiently. Immediately following the contrast media injection the infusion of FDP or glucose was initiated (9-13 min. after induction of anesthesia). The FDP was prepared as a 5% solution and infused at a constant rate of 1.91 ml/min. (97.5 mg/min.) into a main carotid artery. The controls received equal amounts of 5% dextrose via the same route. The analeptic effect of FDP on signs, stages and depth of anesthesia was evaluated by determining the time required for reappearance of eyelid reflex, opening of eyes, deglutition, response to pain, lifting of the head, sitting, and when the animal was able to walk. These data were compared with like date from the group that received 5% dextrose.

The results showed that the time required for return of observable eyelid reflex after beginning the infusion into the carotid artery was $3.70\pm0.67$ min. in the FDP-treated dogs, while for the controls the time was $70.00\pm25$ min. ($\pm$SDM). The time required to regain walking ability was significantly shorter ($76.6\pm16$ min.) in the FDP treated dogs than in the dextrose controls ($295.00\pm24.49$ min.) ($p<0.001$). The table below summarizes the results.

| | Time in minutes after Beginning of Infusion | | | | |
|---|---|---|---|---|---|
| Dog No. | Eyes open | Response To Pain | Lifts Head | Able To Sit | Able To Walk |
| FDP | | | | | |
| 1 | 7 | 17 | 28 | 48 | 60 |
| 2 | 14 | 19 | 33 | 47 | 70 |
| 3 | 5 | 10 | 14 | 35 | 50 |
| 4 | 12 | 18 | 19 | 52 | 95 |
| 5 | 4 | 15 | 20 | 40 | 82 |
| GLUCOSE | | | | | |
| 1 | 80 | 120 | 170 | 300 | 310 |
| 2 | 75 | 130 | 135 | 225 | 300 |
| 3 | 105 | 160 | 190 | 310 | 330 |
| 4 | 54 | 125 | 165 | 215 | 280 |
| 5 | 40 | 100 | 120 | 310 | 265 |

Thus, it can be seen that intra-carotid administration of FDP to animals subjected to thiamylal anesthesia greatly reduces the time required for the animal to regain consciousness and be able to walk. The same analeptic effect, but to a much lesser degree, is observed when FDP is administered systemically. Since FDP has been shown to have profound antishock activity in experimental animals and in man, that phenomenon—taken with the effects of FDP observed in this study—indicates that FDP may have clinical potential in the treatment of barbiturate overdose.

As the results of our tests showed, FDP can successfully be used for blood preservation.

Blood specimens taken from a number of dogs were mixed with FDP in the following proportions: F1-25 mg of FDP per 10 ml of blood and F2-50 mg of FDP per 10 ml of blood. The same proportion was prepared with glucose: G1-25 mg of glucose per 10 ml of blood and G2-50 mg of glucose per 10 ml of blood. The blood specimens were refrigerated for 24 hours and then the blood was tested for ATP content after 24 hours14 days. The table below shows the results of the tests.

| HOLE BLOOD | | |
|---|---|---|
| Time/ATP | F1 | F2 |
| 24 hours | 2.32 m mole/ml | 3.34 m mole/ml |
| 48 hours | 2.34 m mole/ml | 2.08 m mole/ml |
| 7 days | Incubate 30' 37° | |
|  | 0.70 m mole/ml | 2.16 m mole/ml |
| 9 days | 0.82 m mole/ml | 2.04 m mole/ml |
| Time/ATP | G1 | G2 |
| 24 hours | 0.22 m mole/ml | 0.44 m mole/ml |
| 48 hours | 0.32 m mole/ml | 0.34 m mole/ml |
| 7 days | Incubate 30' 37° | |
|  | 0.28 m mole/ml | 0.18 m mole/ml |
| 9 days | 0.26 m mole/ml | 0.40 m mole/ml |
| 14 days | Incubate 40' 37° | |
|  | FDP 1.3 m mole/ml | Glucose 0.88 m mole/ml |
|  | No incubation | |
|  | FDP 1.22 m mole/ml | Glucose 0.40 m mole/ml |

The tests were also conducted under the conditions when 25 mg, 50 mg and 100 mg of FDP were mixed with 10 ml of blood and 25 mg, 50 mg and 100 mg of glucose were mixed with 10 ml of blood. After one night of refrigeration the following results were shown.

| Time/ATP | FDP-25 mg | FDP-50 mg | FDP-100 mg |
|---|---|---|---|
| 24 hours | 1.67 m mole/ml | 2.2 m mole/ml | 2.82 m mole/ml |
| 48 hours | 1.92 m mole/ml | 2.85 m mole/ml | 3.40 m mole/ml |
| Time/ATP | Glucose-25 mg | Glucose-50 mg | Glucose-100 mg |
| 24 hours | 0.475 m mole/ml | 0.375 m mole/ml | 0.250 m mole/ml |
| 48 hours | 0.475 m mole/ml | 0.450 m mole/ml | 0.426 m mole/ml |

The tests were also conducted to investigate the effect of FDP on white blood cells (WBC) on metabolism in vitro. Well-known is the fact that during phagocytosis the energy expenditure of the white blood cells increases as they possess both metabolic pathways, i.e. oxydative metabolism as well as anaerobic glycolysis. It was experimentally assessed whether FDP can stimulate the carbohydrate metabolism of these cells at rest. A similar phenomenon observed for normal human erythrocytes, sickle cells and dog erythrocytes. From healthy humans and dogs, the white blood cells were separated and incubated at 37° Celsius for various periods of time with FDP, glucose and normal saline. At the end of incubation, ATP and intermediates of the glycolytic pathway were assessed. The results indicated that the effect of FDP on carbohydrate metabolism for dog and human WBC is somewhat different. Nonetheless, the ATP production in the WBC from human and canine blood when FDP is added appears to be independent of the concentration (from 5 to 50 mg/ml), but rather a function of the incubation time. However, if AMP or ADP is added to the samples, the increase of ATP becomes a function of the FDP concentration. When human WBC are incubated with FDP the ATP content is 2.47±0.25 m.mole/#WBC, while with the glucose incubated it was 1.28±0.21 m.mole/#WBC. The pyruvic acid concentration in dog WBC incubated with FDP was 10 times greater than those incubated in glucose while those for the human WBC, this difference was of much lesser degree (×2). The dihydroxyacetone (DHA) in the human and canine WBC was 5 to 10 times greater in the FDP incubated than in the glucose ones.

In conclusion, FDP exerts profound stimulating effect on the carbohydrate metabolism of human and canine WBC. This effect might enhance the phagocytic activity of WBC as the latter do expend vast amounts of energy in that process. The eventual practical application would be the use of FDP as a therapeutic agent in sepsis.

The study was also conducted to determine whether IV administration of FDP to dogs subjected to lethal doses of endotoxin will prevent damage to the intestinal mucosa, and death. The rationale was that endotoxin per se and its deleterious effect on hemolate phase acidosis inhibits glycolysis by inactivation of the rate limiting enzyme phosphofructokinase.

Endotoxin shock was produced in dogs by IV injection of *E; coli* endotoxin. Survival of control animals which received glucose and volume replacement was 18% while for those treated with FDP it was 90%.

Figure 5:
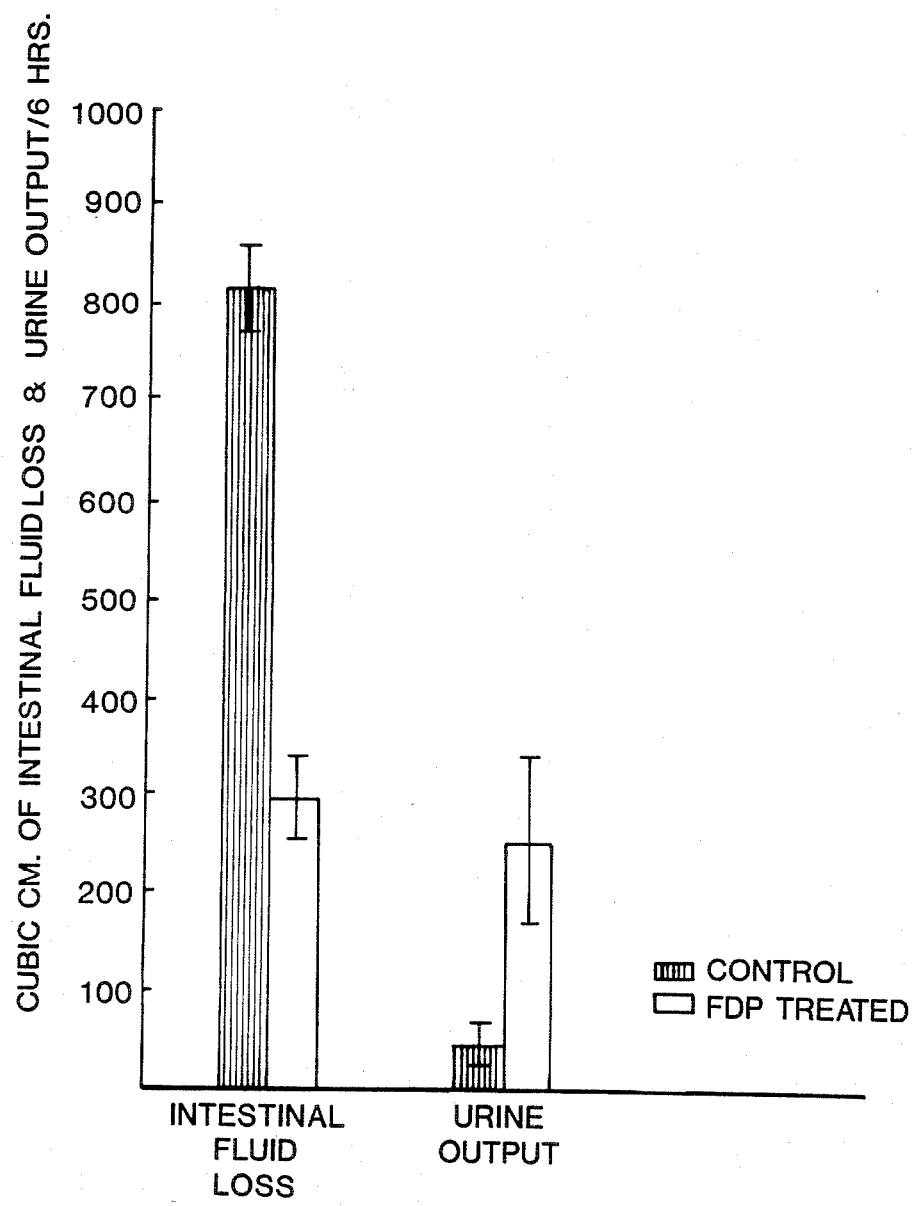
FIG. 5 would illustrate the intestinal fluid loss and urine output of dogs subjected to endotoxin shock.

FIG. 5 is a diagram showing the intestinal fluid loss and urine output of dogs subjected to endotoxin shock. Seven dogs were treated with equimolar FDP and eight received glucose. All animals received fluid supportive therapy (150 ml. of Rheomacrodex and 300 cc. of Lactate Ringer). In all controls there was blood in the fluid lost from the intestine while in the dogs treated with FDP no blood was observed.

Mean arterial pressure of the controls surviving 6 hours of observation was 35%±7.21% below control, while in the FDP treated group it returned to control values between 4 and 6 hours.

Figure 6:
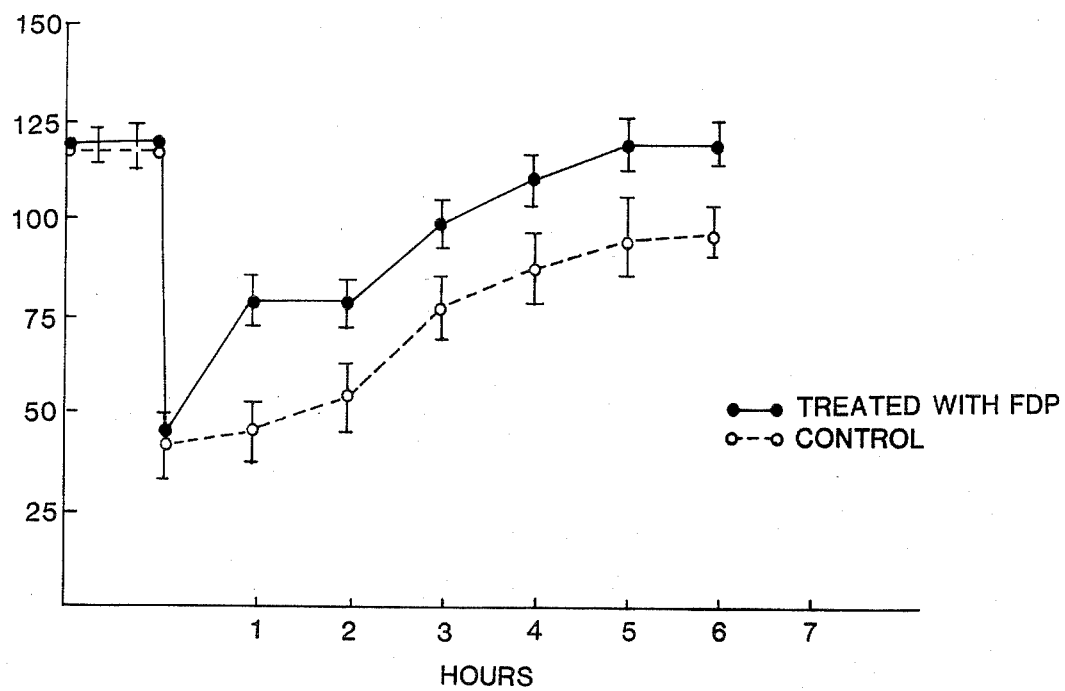
FIGS. 6–7 would illustrate the mean arterial pressure responses of fifteen dogs that received $LD_{90}$ of endotoxin as a bolus IV injection and were supported with fluid theraphy at the same quantity as stated in FIG. 1.
Figure 7:
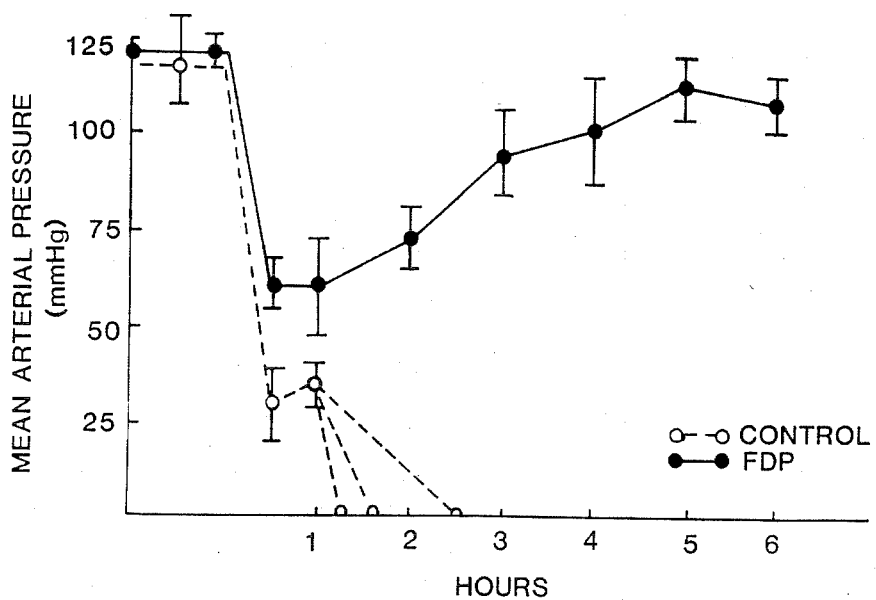

FIGS. 6-7 show the mean arterial pressure responses of 15 dogs that received $LD_{90}$ of endotoxin as a bolus IV injection and were supported with fluid therapy at the same quantity as stated in FIG. 1. Seven were treated with FDP and the controls (8) received equimolar glucose.

It should be noted that FIG. 7 shows mean arterial pressure responses in fluid deprived dogs after IV injection of 1 mg/kg of endotoxin. In three pairs no fluid was given except for the FDP and glucose. The animals that received glucose died within 2½ hours while the ones treated with FDP survived and are still living (five months after the experiment).

All controls had bloody intestinal fluid loss of 830±67 ml/6 hours, while in the treated group no blood was noted and fluid loss amounted to 285±36 ml/6 hours. Urinary output of treated dogs was 276±98 ml/6 hours and that of control group was 46±25 ml/6 hours. In the stomach and intestine of the control group hemorrhagic necrosis of the mucosa was observed while in the group treated with FDP only some vascular congestion was noted. In three pairs no volume replacement was given. The three controls died within 2½ hours while the animals treated with FDP survived.

Administration of FDP to dogs subjected to lethal doses of endotoxin prevents death, intestinal hemorrhage and fluid loss, conserves normal renal function and protects the mucosa of the stomach and intestine from hemorrhagic necrosis.

The attenuation of digitalis toxicity can also be obtained by the administration of FDP.

Dogs subjected to toxic doses of Digoxin were treated with FDP and glucose. FDP administration suppresses significantly the digitalis induced dysarhythmia. Also the dogs treated with FDP survived, while the controls treated with Dextrose 5% died within 3 hours after administration of Digoxin. In this period study 10 anesthesized dogs received 3 mg. IV Digoxin as bolus injection. Five of the dogs received 20 minutes after the Digoxin injection 1 gm. of FDP and then on 2 mg/kg as a constant infusion for the next 3 hours. The five controls received in the same manner Dextrose 5%. The occurrence of dysarhythmia was significantly less in the group treated with FDP when compared to the controls. ($Pi<0.001$.). Moreover, no alternation in hemodynamic parameters such as cardiac output, arterial pressure were noted in the FDP treated group. In the control group prior to the death of the animals there was decline in arterial pressure, vomiting and perfused diarrhea.

Although the exact mechanism by which FDP attenuates the toxic effect of Digoxin cannot be explained at present, this observation might have clinical application in the treatment of digitalis intoxication in man.

This invention provides a method of treatment of practically anyone who is suffering from an injury that had resulted in a loss of blood sufficient to cause their body systems to have a low blood pressure.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method for treating a mammalian subject experiencing myocardial infarction to preserve the subject's ischemic tissue from irreversible tissue damage, comprising:
   administering intravenously to the subject fructose-1,6-diphosphate in an amount of at least 50 mg/kg subject body weight and less than 5 g/kg subject body weight.

2. The method of claim 1, wherein administration is made as a single dose in an amount of 50 mg/kg subject body weight.

3. The method of claim 1, wherein administration is performed intra-aortically.

4. The method of claim 1, wherein administration is by intravenous infusion drip at a rate of from about 1.5 to about 2.0 mg per kilogram of body weight per minute of infusion.

5. The method of claim 3, wherein administration is made in an amount of from 50 mg/kg weight of the subject's heart and less than 5 g/kg weight of the subject's heart.

* * * * *